United States Patent [19]

Wolf

[11] Patent Number: 4,487,055
[45] Date of Patent: Dec. 11, 1984

[54] BREATH ALCOHOL TESTING DEVICE

[75] Inventor: Karl Wolf, Webster Groves, Mo.

[73] Assignee: Alcotek, Inc., Webster Groves, Mo.

[21] Appl. No.: 419,972

[22] Filed: Sep. 20, 1982

[51] Int. Cl.³ .............................................. G01N 1/14
[52] U.S. Cl. .................... 73/23; 73/864.62; 128/719; 128/730; 422/84
[58] Field of Search ................ 422/58, 61, 83–86, 422/90, 98; 436/148; 73/23, 26, 27 R, 863.02, 864.62; 128/719, 730, 204.22, 204.21; 429/25, 34–37

[56] References Cited

U.S. PATENT DOCUMENTS

| | | | |
|---|---|---|---|
| 3,240,068 | 3/1966 | Horeth et al. | 73/864.62 X |
| 3,507,704 | 4/1970 | Webb | 429/34 X |
| 3,966,579 | 6/1976 | Chang et al. | 204/406 |
| 4,297,871 | 11/1981 | Wright et al. | 73/23 |

FOREIGN PATENT DOCUMENTS 1443438 7/1976 United Kingdom .................... 73/23

Primary Examiner—Hiram H. Bernstein
Assistant Examiner—Michael S. Gzybowski
Attorney, Agent, or Firm—Polster, Polster and Lucchesi

[57] ABSTRACT

In a breath alcohol testing device, including a breath-receiving tube, a fuel cell chamber communicating with the tube, a fuel cell within the chamber and a movable wall, for example, a diaphragm, mounted adjacent the fuel cell, to be moved reciprocably between a down position at which the wall is relatively close to the fuel cell and an up position at which the wall is relatively far from the fuel cell, the movement of the wall acting to pump breath to and from the fuel cell, the movable wall defines one wall of the fuel cell chamber, breath in the space between the movable wall and the fuel cell being in substantially unrestricted communication with the fuel cell.

3 Claims, 9 Drawing Figures

BREATH ALCOHOL TESTING DEVICE

BACKGROUND OF THE INVENTION

There is presently on the market a hand-held breath alcohol testing device sold by Intoximeters, Inc., 1901 Locust Street, St. Louis, Mo., under the trademark ALCO-SENSOR. The commercial device and its use are described in a 1982 edition of a manual, of record. A different sampling system for a similar device is described in U.S. Pat. No. 3,940,251.

It had been considered by the developers of the fuel cell type testing device that the adsorbtion of alcohol from a breath sample was substantially immediate and complete. This has been found to be mistaken. In a device such as the Alco-Sensor testing device, the fuel cell requires approximately three to five seconds to obtain complete adsorbtion of the alcohol from the breath sample in immediate proximity to the fuel cell.

It has been desirable in such a system to sweep the surface of the fuel cell with the breath sample as slowly as possible. At the same time, it is necessary to take a sample as nearly instantaneously as possible with the reaching of the deep lung breath of the person being tested and before the person stops blowing. Clearly, these two objects are inconsistent.

In the device described hereinafter as prior art, a breath sample inlet was positioned at one side of a fuel cell chamber and a highly restricted diaphragm pump chamber inlet at the other side. Breath from a sample tube was drawn through the breath sample inlet into the fuel cell chamber, across the fuel cell, and into the diaphragm chamber by the release of a spring-biased button that was holding the diaphram down prior to its release and pulls the diaphram away from the fuel cell upon its release. In spite of the restriction of the diaphragm chamber inlet, to obtain the sample within a reasonable time, the flow across the fuel cell occurred within less than one second. This had two results: first, that between ten and twenty percent of the alcohol in the sample was not adsorbed by the fuel cell but passed into the diaphragm chamber where it was effectively isolated from the fuel cell by the highly restricted opening, and, second, when the diaphragm was depressed to reset the device, the alcohol in the breath expelled from the diaphragm chamber started a new fuel cell cycle, requiring an additive time period, on the order of thirty seconds to two minutes, for purging and stabilizing the fuel cell. The effect of the first result was to require adjustment in the calibration of the individual units, and to make the the amount of alcohol adsorbed depend upon the retrieval rate of the button so that anything that influenced the button action, e.g. temperature change, could affect the calibration accuracy. The effect of the second result is to slow the testing process, particularly undesirable when one wants to run a second test as quickly as possible, for example because the person stopped blowing at the critical time or to check a result that seems anomalous.

Various attempts to resolve the problem have been made, including the provision of internal baffles in the fuel cell chamber to form a labyrinth path across the fuel cell, but they have been found ineffective.

It has now been discovered that by eliminating the diaphragm chamber altogether, making the diaphragm in effect one wall of the fuel cell chamber, complete adsorbtion of the alcohol from the breath sample can be attained in about five seconds, and no re-energizing of the fuel cell is produced when the diaphragm is depressed to prepare the sampling system for another breath sample, reducing the cycle time and increasing the accuracy and sensitivity of the device substantially.

One of the objects of this invention is to produce a breath alcohol testing device that is more accurate and recycles more quickly than such devices known heretofore.

Other objects will become apparent to those skilled in the art in the light of the following description and accompanying drawing.

SUMMARY OF THE INVENTION

In accordance with this invention, generally, stated, in a breath alcohol testing device designed to determine blood alcohol concentrations, the device including a breath-receiving tube, a fuel cell chamber communicating with the tube, a fuel cell within the chamber and a movable wall mounted adjacent the fuel cell to be moved reciprocably between a down position at which the wall is relatively close to the fuel cell and an up position at which the wall is relatively far from the fuel cell, the movement of the wall acting to pump breath to and from the fuel cell, the movable wall, a diaphragm in the embodiment described, defines one wall of the fuel cell chamber, and breath in the space between the diaphragm and the fuel cell is in substantially unrestricted communication with the fuel cell.

DESCRIPTION OF THE PREFERRED EMBODIMENT

Figure 9:
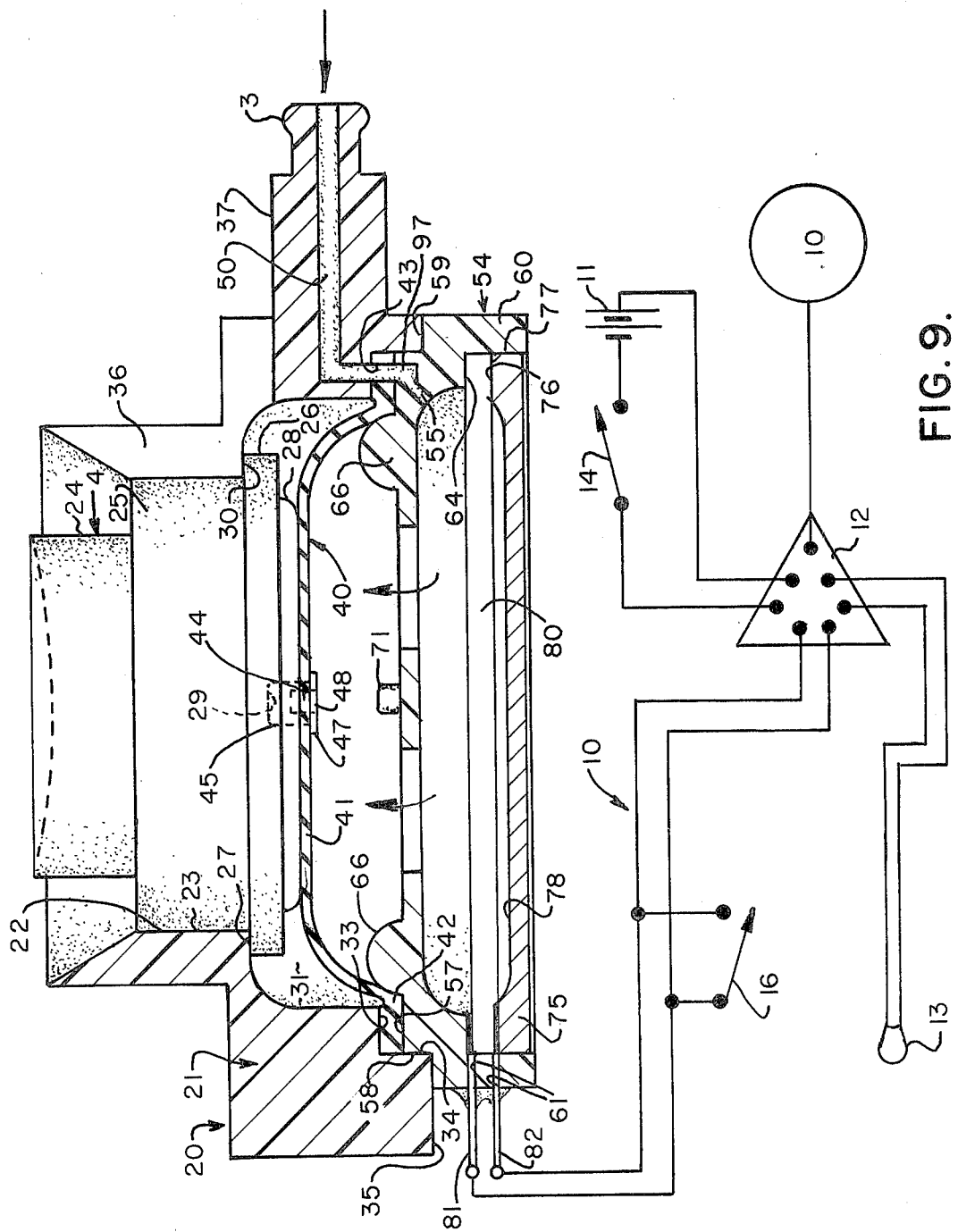
FIG. 9 is a sectional view of a fuel cell of this invention with circuitry shown somewhat diagrammatically.

Referring now to the drawing for one illustrative embodiment of this invention, reference numeral 1 indicates a breath alcohol testing device as it is carried by a law enforcement officer. The device 1 has a case 2, a breath sample tube fitting 3, a set button 4, a read button 5 and a digital meter readout 6, that displays numbers corresponding to the blood alcohol content in percent. Referring to FIG. 9, a circuit 10 includes a battery 11, electrically connected by way of a normally open read button switch 14 to an amplifier 12. A thermistor 13 is electrically connected to the amplifier 12, as are electrodes 81 and 82. A normally open set button switch 16 is electrically connected to conductors from the electrodes 81 and 82 to the amplifier 12 to short out the electrodes 81 and 82 when the switch is closed.

Figure 1:
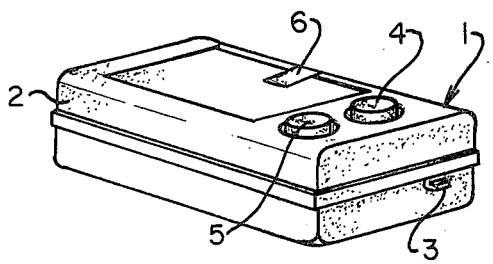
FIG. 1 is a view in perspective of a breath alcohol testing device of this invention.

A sampling system 20, which includes the set button 4, is mounted in the case 2, with the set button exposed as shown in FIG. 1. The sampling system includes a sampling system housing 21 with a set button opening 22 defined by an annular wall 23. The set button as shown in FIG. 9 is circular in plan, and includes a knob 24, a body 25 and a lower, radially outwardly projecting flange part 26 with a flat upper surface forming a shoulder 27. An axially extending concentric lower diaphragm-engaging section 28 of the set button is offset radially inwardly from the flange 26, is rounded at its circumferential wall, flat on its lower surface, and provided with a central socket 29 extending through a flat lower surface.

Internally of the housing 21, the annular wall 23 is stepped radially outwardly downwardly, the first step defining a housing wall shoulder 30 and a diaphragm-receiving cavity 31, and a lower step defining a diaphragm seating shoulder 33, and a fuel cell housing-receiving side wall 34. The lowermost surface of the housing 21 is an annular radial flat 35. A stem 37 of the breath sample tube fitting 3 is, in this embodiment, molded integrally with the housing 21. A notch 36 in the housing is to accommodate a spring, not here shown, by which the set button 4 is biased upwardly to a position at which the shoulder 27 of the button engages the housing wall shoulder 30.

A flexible, impervious diaphragm 40, circular in plan, with a central dome 41 and an annular outwardly radially extending lip 42, has two openings in it, a small inlet passage 43 extending axially through the lip 42, and a connector aperture 44 in the center of the dome 41. A connector 45 has a stem 46, press fit into the socket 29 in the button, a flange 47 in airtight engagement with the inner wall of the diaphragm, and a central guide well 48, opening through the lower surface of the connector and extending into, but not through, the stem 46. The lip 42 of the diaphragm 40 is seated between the shoulder 33 of the housing 21 and an annular ledge 57 of a fuel cell housing 54, with the passage 43 aligned both with a breath sample fitting passage 50 and a hole 97 opening through the upper surface of ledge 57 and communicating with an inlet passage 55. The fuel cell housing 54 has an exterior circumferential side wall 58 stepped radially outwardly downwardly to define a ledge 59 that butts the radial flat 35 when the housing is press fitted into the confines of the seat side wall 34, and a skirt 60. The skirt 60 has radially extending electrode passages 61 through it. The inside surface of the skirt 60 is stepped to provide a fuel cell seat flat 64. A closure 75, with a dished inner wall 78, has an annular fuel cell seat shelf 76 and an outer circumferential edge surface 77 press fit into the confines of the inner surface of the skirt 60. A fuel cell 80 is caged between the seat surfaces 64 and 76. The electrode 81, extending through the upper of the skirt holes 61 is electrically connected to the upper surface of the fuel cell 80 and the lower electrode 82, to the lower surface of the fuel cell.

On the upper surface of the fuel cell housing, contiguous the inner wall of the dome 41 of the diaphragm 40, is an annular bead 66, with a rounded upper surface, around which the diaphragm conforms when it is depressed.

All of the components and their relationships that have been described to this point are common to the prior art Alco-Sensor breath testing device.

Figure 2:
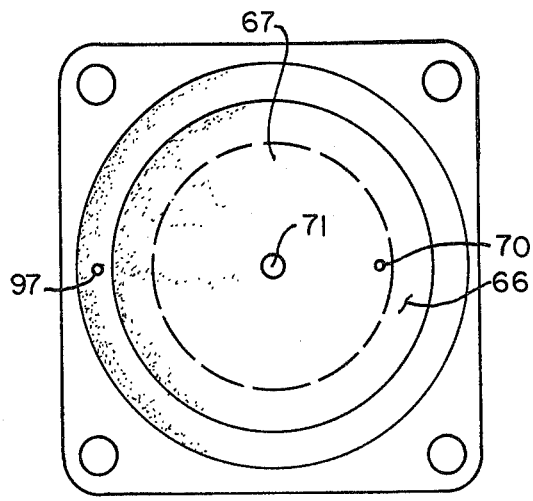
FIG. 2 is a top plan view of a fuel cell housing of the prior art.
Figure 3:
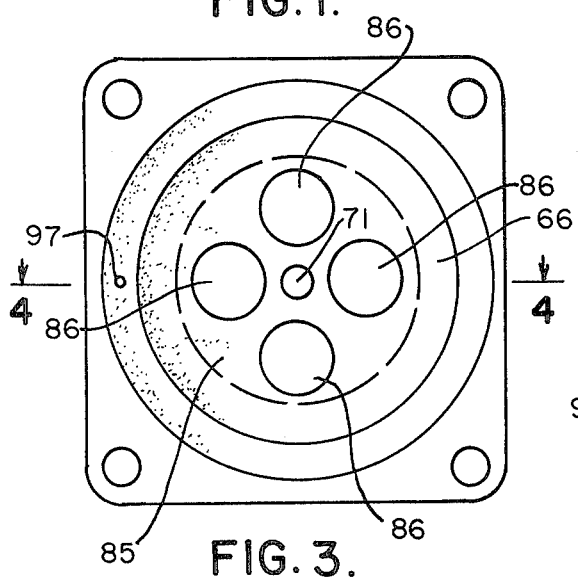
FIG. 3 is a top plan view of a fuel cell housing of one embodiment of testing device of this invention.
Figure 4:
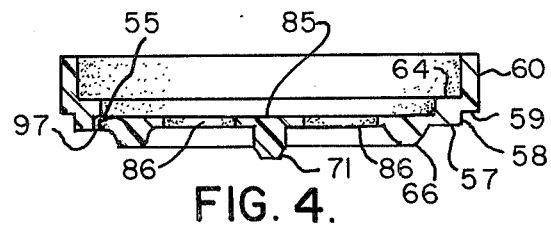
FIG. 4 is a sectional view taken along the line 4—4 of FIG. 3.
Figure 5:
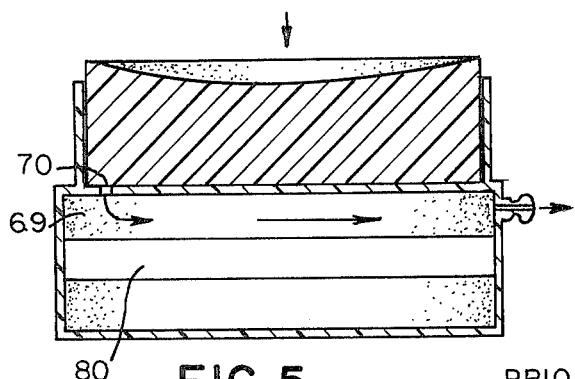
FIG. 5 is a somewhat diagrammatic sectional view of a prior art fuel cell assembly with a set button in its down position.
Figure 6:
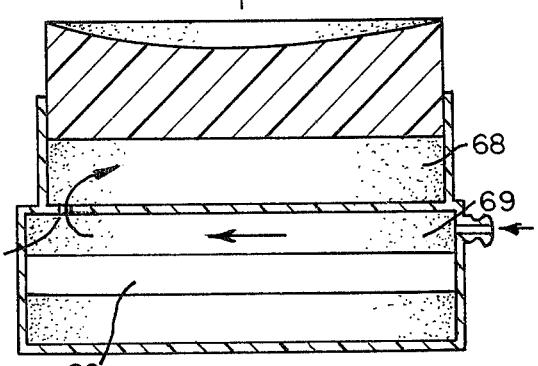
FIG. 6 is a sectional view of the fuel cell assembly shown in FIG. 5 with the set button in the up position.
Figure 7:
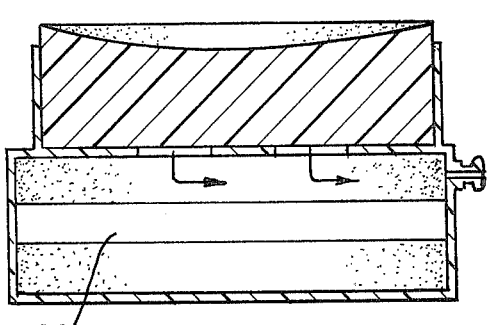
FIG. 7 is a somewhat diagrammatic sectional view of a fuel cell assembly of this invention with the set button in its down position.
Figure 8:
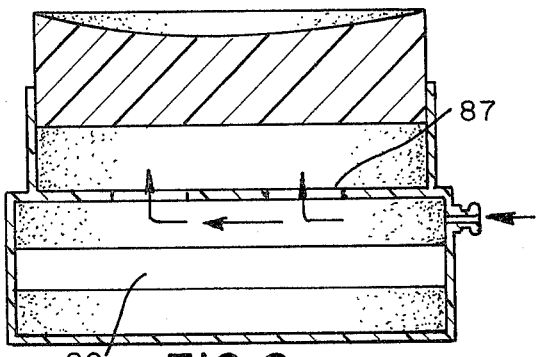
FIG. 8 is a sectional view of the fuel cell assembly shown in FIG. 7 with the set button in its up position.

Referring now to FIGS. 2, 5 and 6, in the prior art device, the fuel cell housing 55 has an upper wall 67 imperforate except for a small diaphragm chamber inlet passage 70. A guide post 71 is integral with and projects upwardly from the center of the wall 67. The wall 67, shown diagrammatically in FIGS. 5 and 6, divides a fuel cell chamber 69 from a diaphragm chamber 68, the two chambers communicating only through the passage 70. The size of the passage 70 (0.5 mm) in the prior art device was such that, as a practical matter, breath in the diaphragm chamber 68 was completely isolated from breath in the fuel cell chamber 69, complete diffusion through the passage 70 requiring on the order of thirty minutes.

In the device of this invention, the wall 67 is replaced by a spider 85, in this embodiment, the sole function of which is to support the guide post 71. Openings 86 between the legs of the spider, are of such a size as to permit unrestricted communication of all of the breath sample with the surface of the fuel cell 80. But for the need, in the Alco-Sensor testing device for the guide post 71 to preclude any cocking of the set button 4 when it is depressed, on account of the use of a pawl engaging the shoulder 27 on only one side when the button is fully depressed, the spider 85 can be eliminated entirely. In either event, the dome of the diaphragm constitutes one wall of a single chamber 87 made up of what in the prior art device are the combined diaphragm chamber 68 and the fuel cell chamber 69.

Because the displacement of the diaphragm in response to the depressing and releasing of the set button 4 remains the same, the amount of sample, of a magnitude of about one cc in the commercial device, remains the same, and no changes in the construction or dimensions of the rest of the device, except for the fuel cell housing wall, need be made. It has been found that, instead of the 80% to 90% of the alcohol in the breath sample's being adsorbed, all of the alcohol in the breath sample is adsorbed in the same length of time, as far as that time can be measured as a practical matter. Not only does this eliminate the error inherent in having less than the full amount of the alcohol adsorbed, but, because no alcohol remains to be adsorbed when the set button is depressed, the fuel cell is no longer re-energized when the button is depressed, and the system recovers rapidly.

The absolute size of the components of the system forms no part of this invention, but merely to give an idea of scale, the fuel cell housing 54 in the commercial device is about 35 mm square, the bead 66, about 19.4 mm i.d., 3.6 mm wide and 1.5 mm high. The guide post is 2.5 mm high and 2.3 mm in diameter, with a 30° taper at its top. The skirt 60 is about 3.0 mm high. The other components are of corresponding scale.

Numerous variations in the construction of the device of this invention within the scope of the appended claims will occur to those skilled in the art in the light of the foregoing disclosure. By way of example, as has been pointed out, the wall 67 may be eliminated completely. To this end, different button retaining means may be employed that do not tend to cock the set button. Different configurations and methods of construction of the buttons, diaphragm and other component parts can be employed. As another example of movable wall, a piston with a face area comparable to that of the diaphragm, slidably mounted in a cylinder with a rolling Teflon seal between them, the piston having a moving surface constituting the movable wall, can be used, but it is more difficult to ensure a seal and uniform operation of the device because of the requirement of the sliding air-tight seal along the piston-cylinder interface. These variations are merely illustrative.

I claim:

1. In a breath alcohol testing device designed to determine blood alcohol concentrations, said device including breath-receiving means, a fuel cell chamber communicating with said breath-receiving means, a fuel cell within said chamber and a movable wall in the form of a diaphragm mounted adjacent said fuel cell to be moved reciprocably between a down position at which the wall is relatively close to the fuel cell and an up position at which the wall is relatively far from the fuel cell, the movement of said wall acting to pump breath to and from said fuel cell, the improvement comprising said movable wall defining one wall of said fuel cell chamber, whereby breath in the space between said movable wall and said fuel cell is in substantially unrestricted communication with said fuel cell, a set button biased away from said fuel cell and mounted to be movable toward and away from said fuel cell, a connector connecting said button to the diaphragm, said connector having a guide well in it opening through a lower surface, a spider between said fuel cell and said diaphragm, and a guide post, carried by said spider and positioned and proportioned to extend into said guide well when said button is moved to its position near said fuel cell, said spider having legs defining between them spaces sufficiently large as to constitute no barrier to unrestricted communication with the fuel cell of breath in the space between the diaphragm and the fuel cell.

2. In a breath alcohol testing device designed to determine blood alcohol concentrations, said device including breath-receiving means, a fuel cell chamber communicating with said breath-receiving means by way of an inlet, a fuel cell within said chamber and a movable wall mounted adjacent said fuel cell to be moved reciprocably between a down position at which the wall is relatively close to the fuel cell and an up position at which the wall is relatively far from the fuel cell, the movement of said wall acting to pump a sample of breath of a predetermined volume to and from said fuel cell chamber, the improvement comprising said movable wall defining one wall of said fuel cell chamber, said movable wall and said fuel cell being in immediate and unimpeded communication with a breath sample entering said fuel cell chamber through said inlet, whereby breath in the space between said movable wall and said fuel cell is in substantially unrestricted communication with said fuel cell.

3. The device of claim 2 wherein the movable wall is a diaphragm.

* * * * *